United States Patent [19]
Ferrieri et al.

[11] Patent Number: 5,808,020
[45] Date of Patent: Sep. 15, 1998

[54] OPTICAL REACTION CELL AND LIGHT SOURCE FOR [18F] FLUORIDE RADIOTRACER SYNTHESIS

[75] Inventors: Richard A. Ferrieri, Patchogue; David Schlyer, Bellport; Richard J. Becker, Islip, all of N.Y.

[73] Assignee: Associated Universities, Inc., Washington, D.C.

[21] Appl. No.: 694,398

[22] Filed: Aug. 12, 1996

[51] Int. Cl.$^6$ .............................. B01J 19/08; C07H 1/00; C07H 5/02

[52] U.S. Cl. .................. 536/18.5; 536/18.4; 536/124; 422/159; 422/186; 422/240; 204/157.15; 204/157.68

[58] Field of Search ................................. 536/18.5, 18.4, 536/124; 204/157.15, 157.48, 157.6, 157.68, 242; 422/159, 186, 240

[56] References Cited

U.S. PATENT DOCUMENTS

| | | | |
|---|---|---|---|
| 4,025,408 | 5/1977 | Marling | 204/163 R |
| 4,165,269 | 8/1979 | Castle | 204/163 R |
| 4,233,493 | 11/1980 | Nath | 219/354 |
| 4,257,860 | 3/1981 | Marling et al. | 204/162 R |
| 4,417,964 | 11/1983 | Wolfrum et al. | 204/158 R |
| 4,578,222 | 3/1986 | Ishikawa et al. | 260/413 |
| 4,617,386 | 10/1986 | Elmaleh et al. | 536/122 |
| 4,672,132 | 6/1987 | Kaneko et al. | 549/311 |
| 5,118,820 | 6/1992 | Hertel | 549/313 |
| 5,169,942 | 12/1992 | Johnson et al. | 536/122 |
| 5,339,255 | 8/1994 | Suzuki et al. | 364/500 |
| 5,382,805 | 1/1995 | Fannon et al. | 250/504 R |
| 5,452,396 | 9/1995 | Soport | 392/416 |

OTHER PUBLICATIONS

Irie, T., et al., *Preparation of $^{18}F$–labeled 6– and 2–fluoro–9–benzylpurine as a Potential Brain–scanning Agent*, Int. J. Appl. Radiat. Isot., vol. 33 pp. 633–636 (1982).

Hamacher, K., et al., *Computer–aided Synthesis (CAS) of No–carrier–added 2–[$^{18}F$]Fluoro–2–deoxy–D–glucose; an Efficient Automated System for the Aminopolyether–supported Nucleophilic Fluorination*, Appl. Radiat. Isot., vol. 41, No. 1, pp. 49–55 (1990).

(List continued on next page.)

*Primary Examiner*—John Kight
*Assistant Examiner*—Howard C. Lee
*Attorney, Agent, or Firm*—Margaret C. Bogosian

[57] ABSTRACT

Apparatus for performing organic synthetic reactions, particularly no-carrier-added nucleophilic radiofluorination reactions for PET radiotracer production. The apparatus includes an optical reaction cell and a source of broadband infrared radiant energy, which permits direct coupling of the emitted radiant energy with the reaction medium to heat the reaction medium. Preferably, the apparatus includes means for focusing the emitted radiant energy into the reaction cell, and the reaction cell itself is preferably configured to reflect transmitted radiant energy back into the reaction medium to further improve the efficiency of the apparatus. The apparatus is well suited to the production of high-yield syntheses of 2-[$^{18}F$]fluoro-2-deoxy-D-glucose. Also provided is a method for performing organic synthetic reactions, including the manufacture of [$^{18}F$]-labeled compounds useful as PET radiotracers, and particularly for the preparation of 2-[$^{18}F$]fluoro-2-deoxy-D-glucose in higher yields than previously possible.

32 Claims, 3 Drawing Sheets

OTHER PUBLICATIONS de Kleijn, J.P., et al., *K$^{18}$F From Reactor–Produced Fluorine–18. Synthesis Of Ethyl 2–Fluororpropionate–$^{18}$F And 4–Toluenesulfonyl Fluoride–$^{18}$F,* Radiochem Radioanal. Letters, vol. 23(3) pp. 139–143 (1975).

Coenen, H.H., *Recommendation for A Practical Production of [2–$^{18}$F]Fluoro–2–Deoxy–D–Glucose,* Appl. Radiat. Isot., vol. 38, No. 8, pp. 605–610 (1987).

Johnson, B., et al., *Synthesis of 2–[$^{18}$F]FDG Using Tetraalkylammonium Bicarbonates,* pp. 582–584.

Guvvala, R., et al., *An Improved Synthesis of No–carrier–added (NCA) 6–[$^{18}$F]Fluoro–L–DOPA and its Remote Routine Production for PET Investigations of Dopaminergic Systems,* Appl. Radiat. Isot., vol. 44, (4), pp. 645–649 (1993).

DeGrado, T., *Synthesis Of 14(R,S)–[$^{18}$F]Fluoro–6–Thia–Heptadecanoic Acid (FTHA).* Journal of Labelled Compounds and Radiopharmaceuticals, vol. XXIX, (9), pp. 989–995 (1991).

Mock, B., et al., *Back–to–Back "One–Pot" [$^{18}$F]FDG Syntheses in a Single Siemens–CTI Chemistry Process Control Unit,* Nuclear Medicine & Biology, vol. 23, pp. 497–501 (1996).

Yang et al. *Fenxi Huaxe,* vol. 21(7):857–860. Abstract Only, 1993.

Krejcik et al. *J. Electroanal. Chem. Interfacial Electrochem,* vol. 317(1–2):179–187. Abstract Only, 1991.

Zhang et al. *J. Electroanal. Chem. Interfacial Electrochem.* vol. 265(1–2):329–334. Abstract Only, 1989.

Nevin et al. *Anal. Chem.,* vol. 60(7):727–730. Abstract Only, 1988.

Nagai et al. *J. Catal.,* vol. 101(2):522–526. Abstract Only, 1986.

OPTICAL REACTION CELL AND LIGHT SOURCE FOR [18F] FLUORIDE RADIOTRACER SYNTHESIS

This invention was made with Government support under contract number DE-AC02-76CH00016, awarded by the U.S. Department of Energy. The Government has certain rights in the invention.

BACKGROUND OF THE INVENTION

The invention relates to apparatus for the chemical synthesis of organic compounds. More specifically, the invention relates to apparatus and methods for radiotracer synthesis, including [$^{18}$F]fluoride-labeled compounds.

Positron emission tomography (PET) is an extraordinarily useful technique for imaging metabolic processes non-invasively. This technique has been employed to study the correlation of metabolism and function in a variety of human pathologies as well as in normal physiological activities. Indeed, PET has proven to be capable of continuously imaging such metabolic processes. Most prominently, PET and appropriate mathematical models have made possible the continuous imaging of brain metabolism, by measuring local cerebral glucose metabolism.

The utility of PET scanning is fundamentally dependent upon the availability of relatively non-toxic radiotracer compounds. The radioisotope of choice has proven to be fluorine-18 ($^{18}$F) because its decay energy (0.64 MEV) allows the highest inherent resolution during PET measurements. Fluorine-18 also has a convenient half-life of 109.7 minutes. An exemplary $^{18}$F-containing PET radiotracer is 2-[$^{18}$F]fluoro-2-deoxy-D-glucose (also known as fluodeoxyglucose F$^{18}$ or 2-deoxy-2-(fluoro-F$^{18}$)-$\alpha$-D-glucopyranose; abbreviated herein $^{18}$FDG). Glucose is readily taken up and metabolized by the brain, and radiolabeled analogues such as $^{18}$FDG are tracers of this behavior. Accordingly, $^{18}$FDG has enabled PET imaging of glucose metabolism in the brain for the localization of epileptic foci, diagnosis of differential dementia, glucose hypometabolism, as well as detection of carcinomas. As a result, $^{18}$FDG has become perhaps the most widely used PET radiotracer.

Several methods of preparing $^{18}$FDG are known in the art. See Coenen et al. (1987). Starting materials for these reactions include various forms of fluorine-18, such as [$^{18}$F]F$_2$, [$^{18}$F]CH$_3$COOF, and [$^{18}$F]F$^-$. Use of [$^{18}$F]fluoride is exemplified by the nucleophilic substitution method of Hamacher et al. (1986), which prepares $^{18}$FDG by means of an aminopolyether-potassium carbonate complex as a phase transfer catalyst for [$^{18}$F]fluoride. Brodack et al. (1988) describe a related method which employs tetrabutylammonium hydroxide as a phase transfer catalyst. Other related methods have been described in U.S. Pat. Nos. 4,617,386 to Elmaleh et al. and 5,169,942 to Johnson et al. The method reported by Ido et al. (1977; 1978) is, by contrast, an electrophilic procedure, using fluorine-18 sources such as [$^{18}$F]acetylhypofluorite. All of these methods, however, are limited in the efficiency by which $^{18}$FDG can be prepared, since the time required to prepare the compound can be on the order of hours, leading to significant losses of the $^{18}$F isotope itself because of its relatively short half-life.

Hamacher et al. (1990) describe an automated apparatus for the chemical synthesis of $^{18}$FDG by nucleophilic substitution. The apparatus includes a single unit reactor, a purification unit, a filling unit, and a computer control unit. This automated apparatus is said to produce yields of $^{18}$FDG of only 40–55%, and employs conventional indirect heating devices.

Moreover, a major problem in meeting increased demands for the $^{18}$FDG tracer is that many cyclotron PET centers have medical cyclotrons which do not have optimal particle energies for $^{18}$F production via the $^{18}$O(p,n)$^{18}$F reaction and other reactions. This imposes a limitation on the capabilities of these centers to synthesize sufficient $^{18}$F for their own needs. As a result, if these centers are to use $^{18}$FDG, they must obtain it from outside sources. Due to the decay of the $^{18}$F, therefore, the institutions purchasing $^{18}$FDG must be located within a 2—3 hour shipping radius of the manufacturing source. It is apparent then, that the development of an improved synthesis of $^{18}$FDG would make it possible for institutions with small medical cyclotrons or other accelerators to produce sufficient quantities of $^{18}$FDG for their own daily use and would allow the production of multiple dose batches of $^{18}$FDG by institutions with cyclotrons of higher production capacity.

Apparatus is known for inducing organic synthetic reactions through the application of certain types of energy to a reaction vessel. A conventional approach long known in chemistry is to apply heat energy to induce (e.g., initiate and/or maintain) a chemical reaction. Apparatus to accomplish this typically heats a reaction vessel by convection or conduction. For example, hot oil baths, resistively heated metal blocks and hot air guns have been employed to heat liquids in appropriate reaction vessels. However, because convection and conduction are indirect heating methods, both necessarily rely on the transmission or propagation of heat through some intermediate physical medium. As a result, these practices can be inefficient as well as time-consuming.

Alternatively, apparatus is known (e.g., U.S. Pat. No. 4,025,408) for applying coherent energy from a laser to excite a specific molecular bond in a reactant to induce a reaction. Another such apparatus is described in U.S. Pat. No. 4,257,860, which uses an infrared laser to excite and dissociate a compound for use in deuterium enrichment. U.S. Pat. No. 4,165,269 describes apparatus which employs a laser, whose light is directed into a tubular reaction vessel in which a mirror is positioned at one end, and a Brewster angle window is positioned at the other. This reaction apparatus is said to be applicable to a reaction in which a sensitizer transduces the laser photons into energy suitable for causing the desired reaction. These methods require a specific wavelength match between the laser and the bond sought to be labilized, accordingly limiting their applicability.

Other methods have also been used to induce certain specific types of reactions. For example, U.S. Pat. No. 4,578,222 describes a method for fluorinating an aliphatic carboxylic acid by means of reaction with a metal through ultrasound irradiation.

In view of the above considerations, it is clear that existing apparatus and methods of organic synthesis, in particular radiotracer compounds such as [$^{18}$F]fluorinated compounds, suffer from inefficiencies, including loss of the specific activity of the compounds by decay during the preparation process, and unduly low yields of the desired compounds. As a result, in the case of PET tracers prepared by conventional apparatus, the compounds suffer from unnecessarily low sensitivity, which impedes diagnostic efficacy.

Accordingly, it is one of the purposes of this invention to overcome the above limitations in apparatus and methods of organic synthesis, and specifically nucleophilic fluorination reactions, by providing a reaction apparatus and method which is highly efficient, permitting production of specific products, such as radiofluorinated tracer compounds in large quantities and having high specific activities.

SUMMARY OF THE INVENTION

It has now been discovered that these and other objectives can be achieved by the present invention, which includes apparatus for performing chemical reactions. The apparatus permits conducting organic synthetic reactions, preferably nucleophilic substitution reactions, and more preferably radiofluorination reactions to provide [$^{18}$F]-containing radiotracer compounds. The invention also includes a method for performing such reactions.

In one embodiment, the invention includes apparatus for performing a chemical reaction. The apparatus includes:
 a) an optical reaction cell including:
  i) a reaction reservoir defining therein a reaction volume capable of containing a reaction medium, and
  ii) an optical window which is substantially transmissive to infrared radiant energy capable of inducing a chemical reaction and which is positioned to permit direct coupling of infrared radiant energy with a reaction medium in the reaction volume; and
 b) a radiant energy supply, including an infrared source capable of emitting broadband infrared radiant energy sufficient to induce a chemical reaction, wherein the radiant energy supply is positioned to directly couple emitted infrared radiant energy with a reaction medium in the reaction volume through the optical window.

Preferably, the infrared source emits radiant energy in a relatively broad band of wavelengths, including wavelengths of from about 0.2 μm to about 2.5 μm. More preferably, the infrared source emits radiant energy having wavelengths of from about 1.4 μm to about 1.9 μm. A highly preferred infrared source is a quartz tungsten halogen lamp.

Preferably, the radiant energy supply further includes an infrared reflector positioned to reflect infrared radiant energy emitted from the infrared source into the reaction volume. More preferably, the reflector is configured to collimate or focus reflected infrared radiant energy into the reaction volume. Accordingly, it is preferred that the reflector has a reflecting surface which describes an ellipsoidal or parabolic shape. The reflector preferably has a reflecting surface made of an infrared reflecting material, preferably gold.

In the apparatus, the reaction reservoir is substantially inert to the contents of the reaction medium in the reaction volume. It is also preferred that the reaction reservoir has an infrared-reflecting surface which is highly reflective to infrared radiant energy passing through the reaction volume. A highly preferred reaction reservoir is made of platinum.

The optical window is preferably highly infrared-transmissive. Preferred materials for the optical window include, for example, quartz.

Due to higher than atmospheric pressures which can result for heating a reaction medium in the apparatus, the optical reaction cell is sealable to prevent release of the reaction medium (as liquid or vapor) from the reaction volume. The apparatus can further include one or more sealable conduits permitting controllable fluid communication with the reaction volume. Moreover, the apparatus preferably further includes a temperature thermocouple for measuring temperatures within the reaction reservoir. Optionally, an output from the temperature thermocouple is electrically connected to a control input of the radiant energy supply to permit temperature-dependent feedback control of radiant energy emission by the radiant energy supply.

Preferred chemical reactions capable of being performed using the apparatus of the invention include endothermic chemical reactions, more preferably nucleophilic substitution reactions, and still more preferably, nucleophilic fluorination reactions.

In another embodiment, the invention includes apparatus for preparing a chemical compound by a chemical reaction, including:
 a) a reaction reservoir including a reaction volume for containing a reaction medium;
 b) a radiant energy supply, including an infrared source for emitting broadband infrared radiant energy sufficient to induce a chemical reaction; and
 c) an optical window substantially transmissive to infrared radiant energy sufficient to induce a chemical reaction,
wherein the reaction reservoir, the radiant energy supply and the optical window are mutually positioned to permit direct coupling of infrared radiant energy emitted from the infrared source, through the optical window, into a reaction medium in the reaction volume.

In a further embodiment, the invention includes reaction apparatus for making a fluorinated compound by a nucleophilic fluorination reaction, including:
 an optical cell, which defines therein a reaction volume for containing a fluorination reaction medium, and which includes an infrared-transparent window through which infrared radiant energy can be directly coupled with a fluorination reaction medium in the reaction volume, attached thereto via a pressure seal;
 a temperature thermocouple fitted to the optical cell for measuring temperature in the reaction reservoir;
 at least one fluid conduit for controllably transferring fluid into or out of the reaction reservoir;
 a vent port for controllably releasing pressure from the reaction reservoir;
 an infrared radiant energy supply positioned to directly couple sufficient broadband infrared radiant energy with the reaction volume, through the infrared-transparent window, to induce a nucleophilic fluorination reaction, wherein the infrared radiant energy supply includes an infrared source for emitting broadband infrared radiant energy and a reflector for reflecting infrared radiant energy emitted from the infrared source into the reaction volume.

In yet another embodiment, the invention includes a method for making 2-[$^{18}$F]fluoro-2-deoxy-D-glucose, including:
 providing a reaction medium including [$^{18}$F]fluoride, a mannose derivative susceptible to nucleophilic fluorination reaction, and an inert solvent in an optical reaction cell adapted to admit infrared radiant energy;
 reacting the [$^{18}$F]fluoride and the mannose derivative in the optical reaction cell by directly coupling broadband infrared radiant energy emitted from an infrared source with the reaction medium to provide an intermediate product by nucleophilic substitution;
 evaporating the inert solvent from the reaction medium; and
 hydrolyzing the resulting intermediate product by contacting the intermediate product with a hydrolyzing agent in an aqueous medium to remove protective groups from the intermediate product to provide a hydrolysis product including 2-[$^{18}$F]fluoro-2-deoxy-D-glucose.

In this embodiment, the reaction medium preferably further includes a phase transfer reagent. Preferred phase transfer reagents include, for example, a mixture of an aminopolyether and an alkali metal carbonate, a tetralkylammonium hydroxide, a mixture of a tetrakylammonium hydroxide and an alkali metal carbonate, a tetralkylammonium carbonate, or a tetraalkylammonium bicarbonate. One highly preferred phase transfer reagent is 4,7,13,16,24-hexaoxa-1,10-diazobicyclo(8.8.8)-hexacosane and potassium carbonate.

The method preferably includes providing [$^{18}$F]fluoride in the form of [$^{18}$F]CsF, [$^{18}$F]RbF, or [$^{18}$F]KF.

Preferred mannose derivatives include, for example, 1,3,4,6-tetra-O-acetyl-2-O-trifluoromethanesulfonyl-D-mannopyranose, methyl 4,6-O-benzylidene-3-O-methyl-2-O-trifluoromethanesulfonyl-β-D-mannopyranoside, a 2,3-O-cyclic sulfate of 1-O-methyl-4,6-benzylidene-β-D-mannopyranoside, 1,6-anhydro-3,4-di-O-benzyl-2-O-triflyl-β-D-mannopyranose, or 1,2-anhydro-3,4,5,6-di-O-isopropylidene-1-C-nitro-D-mannitol.

In the method, the hydrolyzing preferably includes:
reacting the intermediate product with the hydrolyzing agent in aqueous medium under reflux conditions by directly coupling infrared radiant energy emitted from the infrared source with the aqueous medium. Preferred hydrolyzing agents include, for example, hydrogen halides.

In still another embodiment, the invention includes a method for preparing a fluorinated compound, including:
performing a nucleophilic fluorination reaction in an optical reactor including:
a) an optical reaction cell including:
i) a reaction reservoir defining therein a reaction volume containing a reaction medium for conducting the nucleophilic fluorination reaction, and
ii) an optical window which is substantially transmissive to infrared radiant energy capable of inducing the nucleophilic fluorination reaction and which is positioned to permit direct coupling of infrared radiant energy with the reaction medium in the reaction volume; and
b) a radiant energy supply, including an infrared source capable of emitting broadband infrared radiant energy sufficient to induce the nucleophilic fluorination reaction, wherein the radiant energy supply is positioned to directly couple emitted infrared radiant energy with the reaction medium through the optical window.

In this embodiment, the nucleophilic fluorination reaction preferably includes fluorinating using an [$^{18}$F]-containing reagent, and wherein the resulting fluorinated compound is an [$^{18}$F]-fluorinated radiotracer compound. Preferred nucleophilic fluorination reactions include, for example, no-carrier-added nucleophilic radiofluorination reactions for production of [$^{18}$F]FDM, [$^{18}$F]FEDM, [$^{18}$F]-N-methylspiperone, [$^{18}$F]FDG, or [$^{18}$F]FDOPA.

In a further embodiment, the invention is a method for performing a chemical reaction to obtain a reaction product. The method includes:
performing a chemical synthetic reaction in an optical reactor, wherein the optical reactor includes:
a) an optical reaction cell comprising:
i) a reaction reservoir defining therein a reaction volume containing a reaction medium for conducting the chemical reaction, and
ii) an optical window which is substantially transmissive to infrared radiant energy capable of inducing the chemical reaction and which is positioned to permit direct coupling of infrared radiant energy with the reaction medium in the reaction volume; and
b) a radiant energy supply, comprising an infrared source capable of emitting broadband infrared radiant energy sufficient to induce the chemical reaction, wherein the radiant energy supply is positioned to directly couple emitted infrared radiant energy with the reaction medium through the optical window,
thereby providing the reaction product. The method preferably involves an endothermic reaction as the chemical reaction.

Accordingly, it is one of the purposes of this invention to overcome the above limitations in apparatus methods of organic synthesis, and specifically nucleophilic fluorination reactions, by providing reaction apparatus which is highly efficient, permitting faster heating and cooling of the reaction vessel and the reaction medium contained therein. The apparatus of the invention, and the method for its use thereby permit the production of fluorinated compounds in larger quantities, in less time the was previously required Significantly, the apparatus and method of the invention permit the production of radiotracer compounds, such as [$^{18}$F]fluorinated compounds, having higher specific activity than was previously achievable.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein.

DETAILED DESCRIPTION OF THE PREFERRED EMBODIMENTS

The apparatus and method of the invention employ the direct coupling of infrared radiant energy with a reaction medium to induce a chemical reaction. Broadband infrared energy can radiate through space just like light and radio waves and, therefore, can be absorbed directly by, i.e., directly coupled with, a suitable reaction medium. No intermediate physical medium is required in the direct coupling process. The present invention harnesses this phenomenon, which has unexpectedly been found to provide an extremely efficient way of heating a reaction medium, resulting in unusually high yields from chemical reactions such as nucleophilic fluorination reactions.

The apparatus of the invention is capable of inducing a chemical reaction. By "inducing" a chemical reaction it is meant that a chemical reaction is initiated and/or maintained by the direct coupling of infrared radiant energy with a reaction medium in the reaction volume. For example, an exothermic reaction requiring initiation by heating can be performed using the apparatus. More preferably, an endothermic reaction, requiring maintenance of energy input to continue the reaction, can be performed.

An optical reaction apparatus for inducing chemical reactions through direct coupling of infrared radiant energy with a reaction medium has been designed and constructed as described hereinbelow. The optical reaction apparatus includes an optical reaction cell and a broadband infrared light source. The apparatus has general utility for carrying out chemical reactions of numerous types, including endothermic reactions. Preferred reactions capable of being performed using the apparatus include nucleophilic substitution reactions, preferably nucleophilic fluorination reactions, especially radiofluorination reactions involving $[^{18}F]$ fluoride which are of interest for radiotracer preparation in PET. In preliminary studies we have employed this system to directly couple infrared radiant energy with a reaction medium to make $^{18}$FDG rapidly and in high yield.

Figure 1:
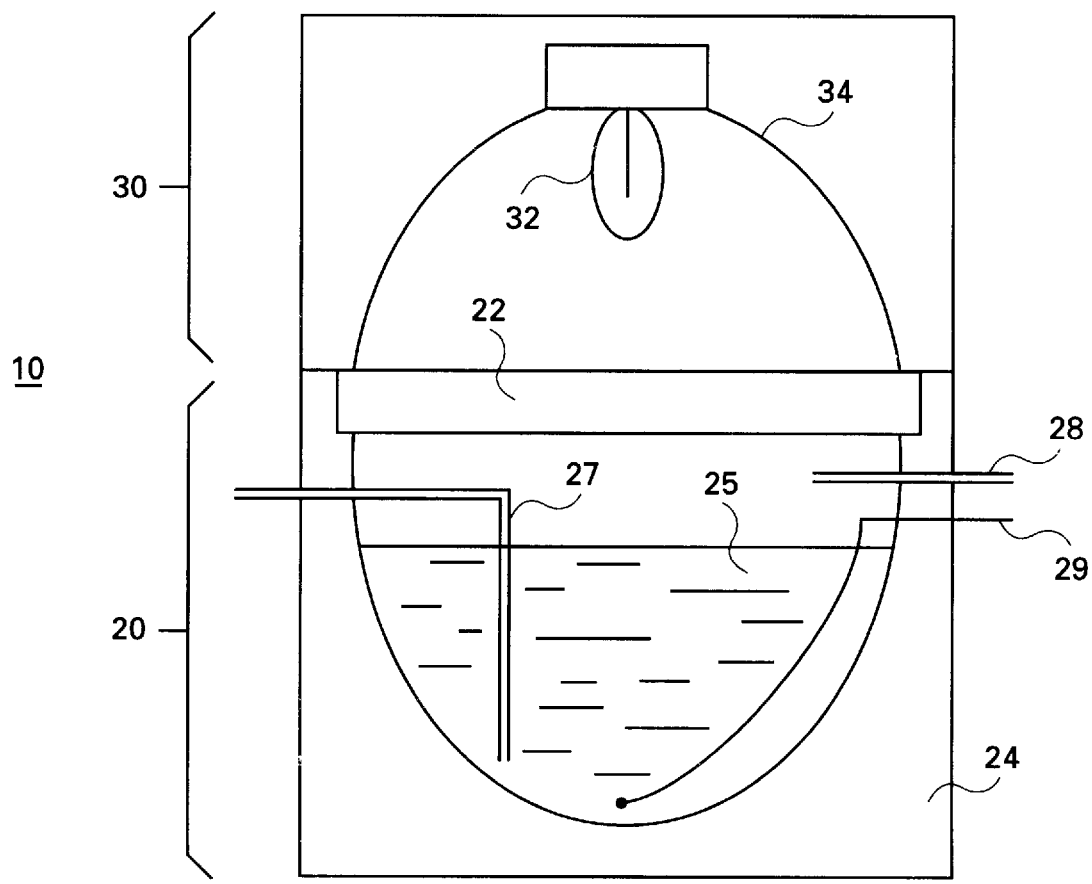
FIG. 1 is a schematic diagram of an optical reactor according to the invention.

FIG. 1 shows a schematic drawing depicting one embodiment of an optical reactor apparatus 10 according to the invention. FIG. 1 shows the orientation of an optical cell 20 relative to a source 30 of broadband infrared radiant energy. The illustrated optical cell 20 includes an infrared-transparent optical window 22 joined (sealed) to a reaction reservoir 24. The infrared source 30, optical window 22 and reaction reservoir 24 are shown in a vertical (preferred) orientation, with the lamp (source) 30 positioned to emit infrared radiant energy downwards through the window 22 and to directly couple the emitted radiant energy with a reaction medium 25 contained in the reaction volume of the reservoir 24. The lamp includes a bulb 32 and a curved reflector 34 to provide both direct and reflected radiant energy, respectively, to the reaction medium 25. Also, a liquid transfer port 27 is shown for controllably introducing liquids into, and removing liquids from, the volume of the reservoir. A vacuum/vent port 28 is provided for controllable inflow and outflow from the volume of gases, such as vapor from the reaction, gas (e.g., helium) overlayers, etc. In addition, a temperature thermocouple 29 is shown for detecting and reporting the temperature of the reaction medium 25 during the course of the reaction.

More generally, in the apparatus of the invention, the optical cell includes a reaction reservoir which defines in its interior a reaction volume capable of containing a chemical reaction medium. The reaction reservoir itself can be made of any material which is compatible with or is substantially inert to the reactants. For example, the reservoir can be constructed of a metal which does not participate (e.g., as a catalyst) in the reaction. Alternatively, the interior surface of the reservoir, which would normally be in contact with the reaction medium, can be coated with a material which is substantially unreactive with the reactants. Polymeric materials having suitable transmissibility to infrared radiant energy, and heat and chemical resistance, can be employed to protect the reservoir or an underlying reflective coating. Platinum is a highly preferred material for manufacturing reaction reservoirs adapted to maintain the fluorination reactions described herein.

Moreover, one of the advantages of the present invention is that the optical cell can dissipate heat quickly following termination of the infrared irradiation. In this way the reaction can be stopped quickly and subsequent processing steps can be performed without excessive delay. Accordingly, to facilitate quick heat dissipation following termination of energy input, the reservoir is preferably manufactured from a material which has high heat conductance. In this case, preferred materials include metals, among which platinum is highly preferred. Cooling can also be accelerated by active cooling means such as a recirculating fluid cooling system.

The need for rapid heat dissipation can be mitigated if the material for reservoir is chosen to have high infrared reflectivity. If an infrared reflective material is employed, then radiant energy which passes through the reaction medium can be reflected back into the medium to further enhance the heating process and thereby enhance the efficiency of the apparatus. In this case little heat is transmitted into the body of the reservoir, and cooling occurs relatively quickly. Again, platinum has excellent infrared reflective characteristics, and is a preferred material for this reason. Infrared-reflecting coatings can also be employed on the interior surface of the reaction reservoir.

In an alternative configuration, the reaction reservoir can be made to have a layered structure, in which the body of the cell is made from one material, e.g., a material having high heat conductance, while a layer of another material, preferably substantially inert and infrared-reflective, is provided on the wall of the reaction reservoir. For example, a ceramic reservoir in which the reaction volume is lined with a metal coating is one possible configuration. Methods are known for depositing metal layers on surfaces, and such methods can be adapted to produce an optical reaction cell having a structure as described herein.

The high temperatures generated within the reaction reservoir of the optical cell can cause volatilization of the reaction medium or components thereof. The direct coupling of infrared radiant energy with the reaction medium can result in the internal temperature exceeding the medium's boiling point, causing the medium to evaporate. The potential for vaporization of the medium becomes especially significant in reactions in which radioisotopes are employed, since the operator must be protected from exposure to such reagents. One solution to this problem would be to seal the cell to prevent release of potentially harmful vapors.

Evaporative loss during reflux could also be accompanied by a receding liquid level in the reaction cell, leaving solid deposits on the walls of the cell. It is possible in this case that the infrared radiant energy might cause some decomposition of the reactants or products. Again, a sealed optical cell can be employed to limit such potential problems. When gas (e.g., nitrogen) is flowed through the optical cell during the reaction, control of the gas flow rate can limit loss of vapor.

However, care must be taken in sealing the cell since the vapor generated from the boiling liquid can translate into rapid and large increases in pressure inside the cell. Accordingly, the construction of the cell should be capable of containing such high pressures. The high tensile strengths of metals render them particularly useful as materials for the construction of the reservoir. Moreover, the joint between the reservoir and the window should not fail under such high pressures. High tensile strength fittings, e.g. mutually threaded steel fittings, can be employed to join the window to the reservoir. Such fittings are commercially available for manufacturing optical cells according to the invention, but for certain configurations appropriate fittings would have to be constructed de novo.

The joint between the window and the reservoir should be sealed to prevent seepage of vapor under heating. Polymeric seals (e.g., o-rings) can be used to effect a seal. Various polymeric materials are suitable for this purpose, and they must generally be heat and chemical resistant. Polytetrafluoroethylene (available, for example, under the trademark TEFLON) is a highly preferred joint-sealing polymer, and o-rings of this material are commercially available.

The optical window of the optical cell is made of any material which is at least substantially transmissive to infrared radiant energy, and which does not substantially interfere with the direct coupling of the emitted radiant energy with the reaction medium. One preferred material is quartz, which is recognized to have excellent infrared transmissivity. Quartz windows (lenses) are available commercially, e.g., stock items from CVI Laser Corporation (Putnam, Conn.). The window is preferably planar, but may have another configuration (e.g., biconvex) depending upon whether any focusing or collimating of the infrared radiant energy is contemplated. The optical window is preferably capable of withstanding the pressures generated within a sealed optical reaction cell during the heating of the reaction medium. Moreover, the window is preferably substantially compatible with the solvents and reactants employed in the reaction medium, since the window desirably maintains its optical characteristics throughout the reaction and can be used more than once before requiring replacement. Filters, coatings, and the like can be applied to or used in conjunction with the optical window to limit delivery of undesirable wavelengths (e.g., ultra-violet) into the reaction volume of the cell.

The apparatus further includes a radiant energy supply mounted to direct infrared radiant energy into the optical cell to enable direct coupling of the radiant energy with the reaction medium. The radiant energy supply can employ any source of radiant energy which generates broadband infrared energy in an amount sufficient to heat a reaction medium to the temperature necessary to induce a chemical reaction. Preferably, the source emits infrared energy sufficient to induce a nucleophilic fluorination reaction, such as reactions for the preparation of $^{18}$FDG.

Preferred infrared sources include quartz tungsten halogen lamps as a light source for rapid heating. Such tungsten halogen lamps will emit radiant energy from about 0.2 $\mu$m to about 2.5 $\mu$m, i.e., wavelengths which range from the ultra-violet into the medium infrared region. Typically, these lamps possess extremely high spectral irradiance in the visible and near or short-wave infrared region peaking at about 0.89 $\mu$m, which is why they are used in projection devices. Water absorbs infrared energy relatively strongly in the near infrared region at about 1.4 $\mu$m and 1.9 $\mu$m and, therefore, couples well with such radiation to provide for rapid heating according to the invention.

It is to be recognized that different media can absorb (i.e., directly couple with) infrared energy to different degrees depending on their chemical and physical characteristics. In addition, absorption is also strongly dependent on the wavelength of the infrared energy used to heat a particular example. Nonetheless, the skilled artisan will appreciate that these considerations do not limit the invention, but are normally resolvable by appropriate matching of the physical characteristics of the infrared source and the reaction medium, all of which can be determined by conventional means and/or by taking advantage of the technical literature.

It is an important feature of the invention, however, that the infrared source be capable of emitting broadband infrared radiant energy, i.e., infrared energy (typically non-coherent) in which at least a substantial portion of the total emitted energy is in the relatively broad band of wavelengths in the short to medium wave infrared range (i.e., 0.76 $\mu$m to 4.0 $\mu$m). The infrared source useful for the invention, therefore, is distinguished from infrared lasers which emit coherent light of a single wavelength, and infrared diode lasers which exhibit some spectral broadening but which still have extremely narrow spectral profiles.

One preferred example of a commercially available infrared source useful in the apparatus of the invention is a quartz tungsten halogen lamp General Electric model ELH 120 V, with a 300 W projector bulb from Bulbtronics, Farmingdale, N.Y. This lamp is manufactured with an integral ellipsoidal reflector made of a dichroic material (i.e., mirrored aluminum deposited on quartz with a silicon monoxide overlayer). Such an arrangement serves to focus the radiant energy through reflection to a point external to the source. This lamp yields a spot curve with a diameter of about 8.9 mm full width at half maximum (FWHM) at a point 35 mm from the forward edge of the reflector. A standard AC power supply can be used to power the infrared source. Preferably, the power can be modulated to control the amount of radiant energy emitted into the optical cell, thereby permitting control of the temperature within the cell. In one preferred embodiment, the power supply is modulated by means of feedback (e.g., negative feedback) from the temperature thermocouple, permitting direct and automated control of temperature.

Typically, the dichroic coating on the integral reflector of this type of lamp is designed to maximize reflection of ultra-violet and visible light while transmitting infrared radiation. In the present invention, however, the lamp reflector is preferably modified to increase infrared reflectivity. This can be accomplished by providing an infrared-reflecting coating on the reflector surface. For example, a infrared-reflecting metal such as gold can be deposited by any known technique onto the surface. Deposition of a coating of gold about 300 $\mu$g/cm$^2$ (~1554 Å) thick has been found to be effective for increasing infrared reflectance. Other coating materials having high infrared reflectance can also be used. Such coatings are desirably deposited while maintaining the mirrored finish integrity of the reflector, but the surface is modified to reflect and focus much more of the infrared energy than would otherwise be possible.

The orientation of the optical cell relative to the infrared source is not critical. For example, the source can be positioned below the reservoir to emit the radiant energy upward into the reaction volume of the cell. Horizontal orientation is also possible, but may be less preferred if the level of the reaction medium fluctuates or cavitation during heating disrupts consistent coupling of the radiant energy with the reaction medium. A more preferred orientation is that in which the infrared source is positioned vertically over the optical cell, with the reaction medium contacting the walls of the reaction reservoir rather than the optical window (or the sealing gasket if any). Preferably, the components of the apparatus are positioned to evenly distribute the radiant energy throughout the reaction medium. Accordingly, the infrared source, the optical window and the reaction reservoir are preferably all aligned along a single axis. Preferably, the components are aligned to exhibit substantial radial symmetry, e.g., a cylindrical conformation.

The efficiency of the method of the invention appears to be strongly dependent on the lamp's focal point positioning relative to the bulk of the reaction medium in the reaction volume of the optical cell. That is, by focusing the emitted and reflected radiant energy to a spot within the reaction volume, it is possible to concentrate the radiant energy, and thereby increase the radiochemical yield in the final product. Accordingly, it is preferred that the infrared energy be focused, more preferably focused such that the focal point of the emitted radiant energy is within the volume occupied by the reaction medium during the reaction.

The optical reactor apparatus of the invention is capable of being employed to perform chemical reactions more efficiently than has been practicable heretofore. In particular, the invention can be employed to initiate and maintain endothermic chemical reactions, including nucleophilic substitution reactions ($S_N2$). Alternatively, any other chemical reaction requiring heat input at any point can be performed using the apparatus, including exothermic reactions which proceed spontaneously after initiation by an energy input.

The apparatus is particularly well adapted for use in nucleophilic fluorination reactions, including such fluorination reactions as radiofluorinations using fluorine-18. An especially preferred application of the optical reactor apparatus is the synthesis of $^{18}$FDG in higher radiochemical yield and with higher specific activity than has previously been possible.

Certain methods for the production of $^{18}$FDG are known in the art. Of particular utility are the methods which yield $^{18}$FDG from [$^{18}$F]fluoride via nucleophilic substitution reactions (i.e., $S_N2$ reactions). These methods make more effective use of [$^{18}$F]fluoride, having a theoretical yield of 100%. Moreover, the $S_N2$ reaction using a D-mannose precursor can yield epimerically pure $^{18}$FDG. The preparation of $^{18}$FDG according to the invention preferably uses the synthetic method developed by researchers at the Jülich Laboratory in Germany (Hamacher et al. 1986). This preferred method uses 1,3,4,6-tetra-O-acetyl-2-O-trifluoromethanesulfonyl-D-mannopyranose (also known as mannose triflate) reacted with no-carrier-added [$^{18}$F]fluoride in conjunction with the 2.2.2 cryptand, 4,7,13,16,24-hexaoxa-1,10-diazobicyclo(8.8.8)-hexacosane (commercially available under the trade name KRYPTOFIX 2.2.2, from Aldrich Chemical Co., Inc., Milwaukee, Wis.) to enhance fluoride reactivity.

Mannose triflate is a highly preferred precursor substrate for the production of $^{18}$FDG by nucleophilic fluorination. Other precursor substrates have been described which are also useful in nucleophilic substitution reactions capable of improvement in accordance with the present invention. Such other precursors include, for example, the 2-triflate of 1,3-di-O-methyl-4,6-O-benzylidene-β-D-mannopyranose, the 2,3-O-cyclic sulfate of 1-O-methyl-4,6-benzylidene-β-D-mannopyranoside, 1,6-anhydro-3,4-di-O-benzyl-2-O-triflyl-β-D-mannopyranose, and 1,2-anhydro-3,4,5,6-di-O-isopropylidene-1-C-nitro-D-mannitol.

The nucleophilic fluorination reaction is benefited by inclusion in the reaction medium of a phase transfer reagent. Any conventional phase transfer reagent can be used. Suitable phase transfer reagents include, for example, salts which provide tetraalkylammonium counterions in solution to enable reaction of the triflate reagent with the fluoride ion. Examples of suitable phase transfer reagents include, without limitation, mixtures of a tetraalkylammonium hydroxide and an alkali metal bicarbonate, tetraalkylammonium bicarbonates, tetraalkylammonium carbonates, and mixtures thereof. The alkyl group in these compounds can be any otherwise saturated hydrocarbyl $C_1$–$C_4$ radical, including ethyl and butyl groups. The alkali metal bicarbonate can be a carbonate of any alkali metal, preferably the carbonate of potassium ($K_2CO_3$). Among mixtures of tetraalkylammonium hydroxides and alkali metal bicarbonates, a preferred phase transfer reagent is KRYPTOFIX 2.2.2-$K_2CO_3$. Several suitable phase transfer reagents are described in U.S. Pat. No. 5,169,942 to Johnson et al.

In the synthesis of $^{18}$FDG, the intermediate product obtained from the nucleophilic fluorination reaction is then hydrolyzed. A hydrolyzing agent is typically provided in an aqueous medium to remove the protective groups from the intermediate product. The product of the hydrolysis is 2-[$^{18}$F]fluoro-2-deoxy-D-glucose. The hydrolyzing agent is any compound which is effective to hydrolyze the protective groups without otherwise modifying the intended product or substantially interfering with its production. Preferred hydrolyzing agents include, for example, hydrogen halides, more preferably, hydrochloric acid. Boron halides may in certain limited circumstances be useful as hydrolyzing agents, but these are generally less preferred since the boron cation can cause problems during the purification step of the fluorinated product. Boron halides, although solid, dissolve upon contact with an aqueous medium to yield the corresponding hydrogen halides. Alternatively, in the case of the hydrolysis of ester products, aqueous bases can be employed, such as potassium hydroxide (KOH) and other strong sources of hydroxide ions (OH$^-$) (DeGrado 1991).

Other nucleophilic substitution reactions besides $^{18}$FDG synthesis can be performed to obtain other [$^{18}$F]fluorinated compounds. For example, methods are known for the production of [$^{18}$F]fluoro-deoxymannose ([$^{18}$F]FDM), [$^{18}$F] fluoroethyl-deoxymannose ([$^{18}$F]FEDM), and [$^{18}$F]-N-methylspiperone. Other methods include a method for the production of 14(R,S)-[$^{18}$F]fluoro-6-thia-heptadecanoic acid ([$^{18}$F]FTHA) (DeGrado 1991), and a method for the production of 6-[$^{18}$F]fluoro-L-dopa ([$^{18}$F]FDOPA) (Reddy et al. 1993). The apparatus of the invention is particularly well suited to the performance of such no-carrier-added nucleophilic radiofluorination methods, inasmuch as these syntheses can be performed quickly to improve the specific activity of the radiofluorinated product. Moreover, emissions of radioisotopes and other toxic products can be effectively contained within the sealed apparatus. Of course, these and other related fluorination reactions can also be performed using fluorine-containing reagents which are substantially free of $^{18}$F, since these reactions proceed independent of the fluorine isotope being employed.

Several commercial instruments have been marketed which carry out $^{18}$FDG synthesis in an automated fashion using conventional heating sources. See, e.g., Hamacher et al. (1990). Typically, radiochemical yields of $^{18}$FDG are about 55%, decay corrected to the end-of-bombardment (EOB) with radiochemical purities exceeding 98%. Synthesis times generally take between 40 and 60 minutes depending on the commercial system. Thus, uncorrected yields (end-of-synthesis, EOS) range between 35% and 42% for the commercial systems. By contrast, the apparatus of the invention now enables EOS yields for the reaction of at least about 45%, and have proven capable of EOS yields exceeding 60%.

The optical reaction apparatus of the invention is capable of being incorporated into an automated system for remotely producing the desired reaction product. For example, automated reaction systems for the generation of $^{18}$FDG are known (e.g., Hamacher et al. 1990), but such systems use conventional (indirect) heating elements which suffer from the inefficiencies mentioned previously. As another example, Reddy et al. (1993) describe a remotely operated system for synthesizing [$^{18}$F]FDOPA. By substituting the optical reaction apparatus of the invention for the reaction vessel and heating systems in such automated and remotely-operated systems, radiofluorination reactions can be performed with much higher efficiency and radiochemical yield than would otherwise be possible with those types of systems.

An automated optical reaction system in accordance with the present invention typically includes a number of components. For example, a plurality of reservoirs, containing various reagents and other liquids (e.g., acetone wash), can be provided along with conduits and valves for controlling the delivery of each liquid as needed into the reaction volume of the cell. The reaction reservoir can include one or more valved conduits for permitting fluid transfer into and out of the reaction volume. The reaction reservoir can also include a vent/vacuum port. A temperature thermocouple can be provided to monitor reaction volume temperature, preferably also being integrated (e.g., providing feedback, preferably negative feedback) into a power supply system for the infrared source to modulate the level of radiant energy being supplied into the reaction volume. Fluids, including the reagents, the reaction medium, and gases such as helium, nitrogen, etc., can be displaced throughout the communicating conduits (e.g., TEFLON tubing) by positive (e.g., pressurized air or other gas) and/or negative (e.g., vacuum) displacement means. Alternatively, mechanical pumps, such as motorized syringes, can be employed to drive the fluids. Electronically operable (e.g., solenoid) valves are available which can be employed to enable remote control over which of the conduits are in communication at any given time. Purification columns can also be included, e.g., ion exchange media, alumina, filters, etc., to permit the isolation of highly purified product. This is especially critical in the production of PET radiotracers for clinical use in humans. The entire automated system and its components can be monitored and controlled by a programmable logic control system, such as a microcomputer with dedicated software.

The following examples are provided to assist in a further understanding of the invention. The particular materials and conditions employed are intended to be further illustrative of the invention and are not limiting upon the reasonable scope thereof.

EXAMPLE 1

Figure 2B:
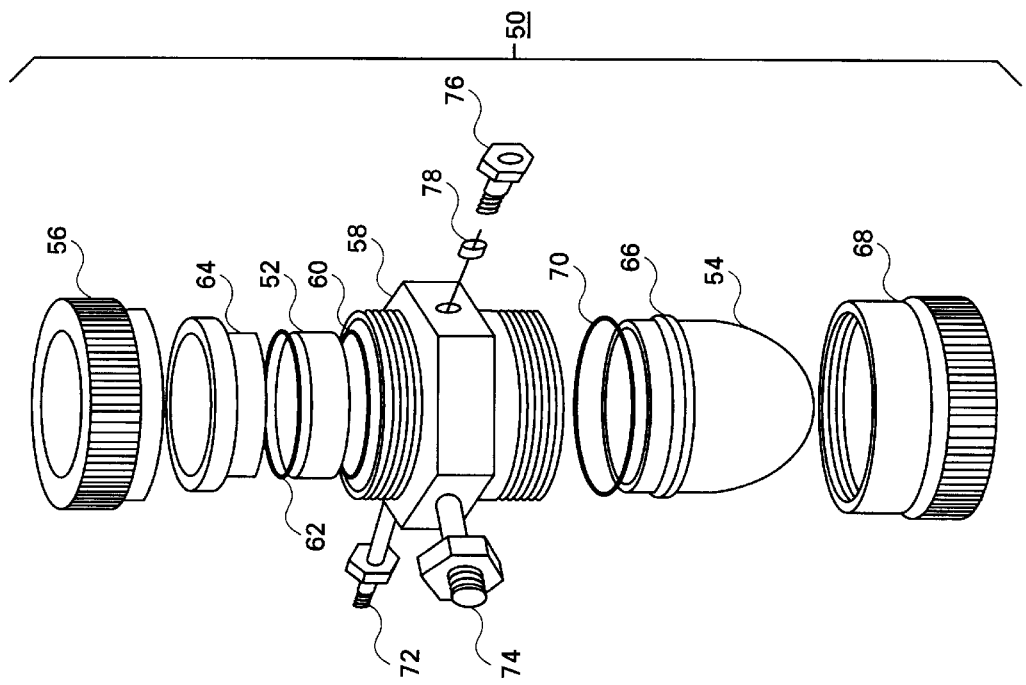
FIG. 2B is an exploded view of the optical cell portrayed in FIG. 2A.
Figure 2A:
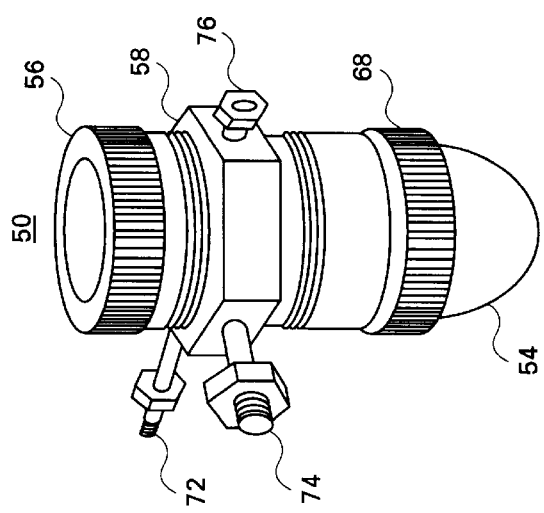
FIG. 2A is a three-dimensional view of one example of an optical cell according to the invention.

An optical cell was built in accordance with the present invention as described generally hereinabove. The optical cell is illustrated in FIG. 2A, which provides a 3-dimensional representation of the assembled optical cell. FIG. 2B is an exploded view of the disassembled components of the optical cell illustrated in FIG. 2A. The described cell is compact and rugged, and can be quickly disassembled and reassembled without the need for any tools.

Referring now to FIGS. 2A and 2B, in the illustrated cell 50, a 1" diameter Cajon Ultra-Torr union (316 stainless steel) was used to mate an optical window 52 to a platinum reaction reservoir 54. Both threaded ends of the union 58 were shortened by ⅛". In addition, the inside steps of the union 58 were cut to create perpendicular angles with the inside walls. The top cap 56 (and threads thereof) of the union was also shortened to permit a gas tight seal against the optical window 52. The optical window 52 was a standard stock item from CVI Laser Corporation (Putnam, Conn.), made of BK-7 quality quartz for high transmission of light from the ultra-violet region into the infrared. The window 52 had dimensions of 1"×¼", which allowed it to slide easily inside the body 58 of the Ultra-Torr union and rest on an internal step therein. A gas-tight seal was made between the window 52 and the union body 58 using a gasket 60 made from 20 mil thick Teflon sheet. A top gasket 62 was also used in order to protect the window 52 from the top ferrule 64. The top ferrule 64 of the union was replaced with an elongated version in order to create a tight fit once the cap 56 was screwed down.

A standard stock 10 mL volume platinum crucible (Scientific Products Division, Baxter, Inc., McGaw Park, Ill.) was used as the reaction reservoir 54. The crucible was silver-soldered to the standard stainless steel ferrule 66 that came with the Ultra-Torr union. The ferrule 66 was mounted in reverse. No modifications were made to the ferrule 66 or bottom cap 68. A gas-tight seal was made between the ferrule-vessel assembly (54+66) and the union body 58 using a 20 mil thick TEFLON gasket 70.

The body 58 of the Ultra-Torr union was modified to accommodate three ports. Two ports, possessing ¹⁄₁₆" and ⅛" stainless steel Swagelok fittings 72 and 74, were silver-soldered to the nut portion of the union body. The ¹⁄₁₆" Swagelok port allowed for insertion of a ¹⁄₁₆" o.d. stainless steel sheathed temperature thermocouple (J-Type thermocouple, not shown; from Omega Inc., Stamford, Conn.) down into the reaction reservoir 54. The ¹⁄₁₆" Swagelok fitting 72 was bored out to accommodate this probe. A gas-tight seal was made between the probe's sheath and the Swagelok fitting 72. The ⅛" Swagelok port 74 allowed for connection to a ⅛" TEFLON tube (not shown) that could either be connected to a vacuum or simply vented depending on the needle. The third port consisted of a ⅜" deep hole that was tapped to accommodate a 10–32 threaded HPLC nut 76 (Alltech Associates, Inc., Deerfield, Ill.). The inner recess of this hole was drilled through the body 58 of the union, and was large enough to accommodate a 20 gauge needle 78. Liquid transfer to and from the reservoir 54 was accomplished using a Hamilton RN-type syringe needle 78 (Alltech Associates, Inc.) that was pushed through the hole. The shaft of the needle 78 could be bent as it was pushed through the port 76 so that it extended down to the bottom of the platinum vessel 54 once assembly was complete. This type of needle is characterized by the small stainless steel button that is welded to the shaft of the needle. A gas-tight seal was made between this button and ¹⁄₁₆" o.d. TEFLON tubing (not shown) by flaring the end of the tubing after it was passed through the HPLC nut 76. The flaring was performed easily using an Omnifit flaring tool (Alltech Associates, Inc.). The nut 76 compressed the tube against the backside of the needle button as it was tightened into the hole. Finger tightening only was necessary to achieve an adequate seal. This design allows for rapid and easy exchange of the needle port if it should fail due to plugging.

EXAMPLE 2A

The optical cell of Example 1 was fitted with an infrared source, by clamping the cell to one of four legs used to support the source in an inverted position. The infrared source was a quartz tungsten halogen lamp General Electric model ELH 120 V, with a 300 W projector bulb obtained from Bulbtronics, Farmingdale, N.Y. This lamp was manufactured with an integral ellipsoidal reflector made of a dichroic material (i.e., mirrored aluminum deposited on quartz with a silicon monoxide overlayer). Such an arrangement serves to focus the radiant energy through reflection to a point external to the source. This lamp had a 35 mm focal point generating about a 9 mm spot at that distance. The power supply for the lamp was an AC phase control module manufactured by Omnetics (Syracuse, N.Y.), part number 602-A. (An alternative power supply is the PHS series AC phase controller manufactured by SSAC, Inc. (Baldwinsville, N.Y.).)

EXAMPLE 2B

Another infrared emitting lamp was prepared to have increased infrared reflectance. A lamp identical to the lamp described in Example 2A, was modified to provide the reflecting surface with a gold coating. A layer of gold of about 300 μg/cm² (~1554 Å) was deposited by vapor deposition in a vacuum. In this way the reflector was provided with full infrared reflecting capability. It was found that the total emitted radiant energy from this lamp (directly emitted and reflected) was increased by about 50% as measured by the decreased time required by the modified lamp to evaporate to dryness 1.5 mL of water (See Example 3, below).

EXAMPLE 3

The apparatus described in Examples 1, 2A, and 2B was tested for its efficiency in drying aqueous media. One of the reasons for this test is that typically the first step in any radiofluorination reaction using [$^{18}$F]fluoride is to dry the aqueous phase. This is because nucleophilic displacement reactions involving [$^{18}$F]fluoride proceed more efficiently in nonaqueous environments. By virtue of the way the fluorine-18 radionuclide is produced in the cyclotron target, the isotope is processed and delivered in an aqueous carbonate solution. Its chemical form under these circumstances is the fluoride ion ($F^-$). Notwithstanding these features peculiar to such radiofluorination procedures, the drying test provides a general indication of the overall efficiency of the apparatus.

Drying profiles were measured using the temperature thermocouple attached to the optical cell. The sensing end of the thermocouple extended down into the liquid volume residing in the reaction reservoir of the platinum cell. During drying, the cell was vented and a stream of helium gas was passed through a liquid transfer needle also affixed to the cell. The helium flowrate was maintained at a constant rate (100 mL/min) through all measurements. When a liquid is boiling, the thermocouple will read the temperature of the liquid, which remains substantially constant (the boiling temperature) as long as there remains liquid enough to measure. However, when all of the liquid has been driven off, the temperature in the reservoir increases quickly, reflected as an abrupt increase in the thermocouple output. Accordingly, the temperature thermocouple response was used as an indicator of vessel dryness.

Figure 3:
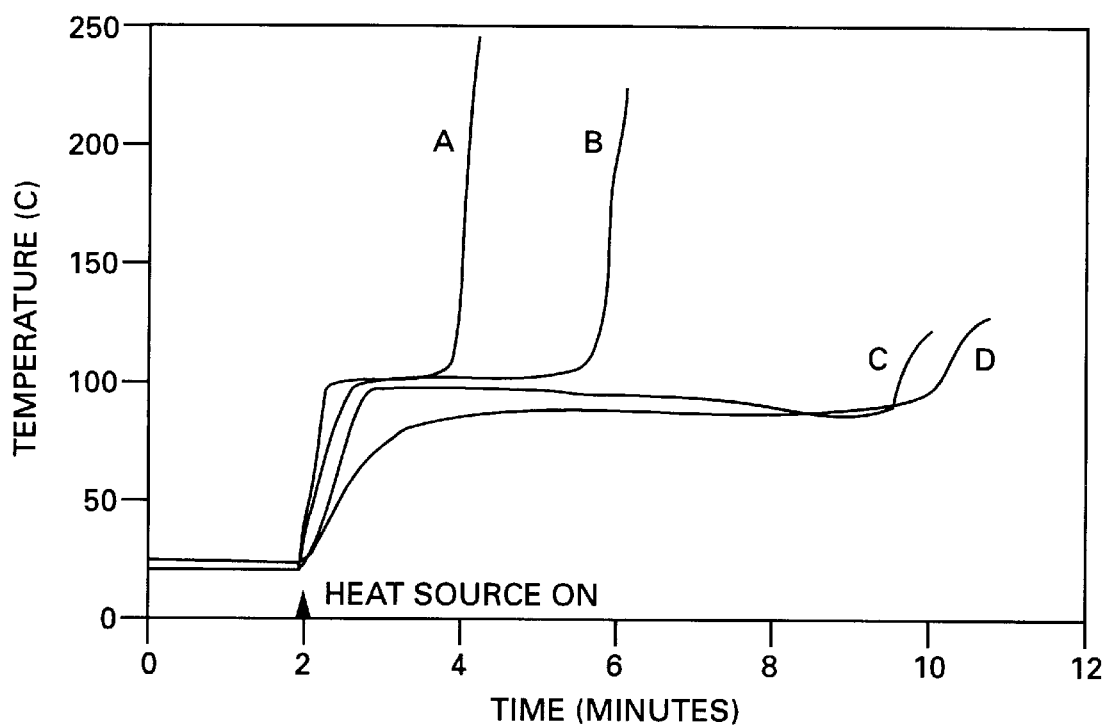
FIG. 3 is a graph showing drying profiles for a given volume of water comparing heat sources.

FIG. 3 shows results from measurements in a comparison of drying profiles of 1.5 mL of water using several different energy sources. Trace A and Trace B report temperature using a halogen lamp (designated NIR for near infrared source). Trace A illustrates the performance of the lamp with full infrared reflecting capability (i.e., gold-coated lamp of Example 2B), while Trace B illustrates lamp performance using partial infrared reflecting capability (i.e., unmodified lamp of Example 2A). Comparisons were also made to conventional heating sources such as a hot oil bath operated at 180° C. (Trace C) and a 450 Watt hot air gun (Trace D) operated at full power.

FIG. 3 clearly shows that the apparatus of the invention is an efficient means of heating a liquid such as a reaction medium. Specifically, the apparatus of the invention (Trace A) was about 75% more efficient than either of the conventional heating sources (Traces C and D). FIG. 3 also shows that the apparatus using a light source with full infrared reflector (Trace A) was 50% more efficient than the apparatus using an unmodified lamp/reflector (Trace B).

EXAMPLE 4

Synthesis of 2-[$^{18}$F]fluoro-2-Deoxy-D-Glucose ($^{18}$FDG)

Using a protocol substantially corresponding to the conventional synthetic methodology described hereinabove (Hamacher et al. 1986), an optical cell and light source according to the invention were used to synthesize $^{18}$FDG.

First, [$^{18}$F]fluoride was dried over 0.6 mL of 0.01M $K_2CO_3$ mixed with 0.5 mL of acetonitrile, 25 mg of KRYPTOFIX, and an additional 4 mg of $K_2CO_3$. The lamp was operated at full power until the temperature in the cell, as measured by the thermocouple, began to rise drastically. Care was taken never to allow the temperature to rise above 120° C. to ensure minimal thermal decomposition. This step took less than 30 sec. Dry nitrogen gas was passed through the cell at 100 cc/min during this process, while at the same time the cell was evacuated through a dry ice condenser. We allowed the lamp to operate for an additional 2 min at 30% power to insure that no liquid droplets remained in the upper portion of the cell.

The labeling step was carried out under reflux in 2 mL of acetonitrile containing 30 mg of mannose triflate for 5 min. The lamp was operated at 30% power for this step. The temperature within the cell never exceeded the boiling point of the solvent.

Hydrolysis of the tetraacetyl [$^{18}$F]fluorodeoxyglucose intermediate was carried out to completion within 10 min while under reflux in 3 mL of 2N HCl. Again the lamp was operated at 30% power for this operation.

Following synthesis, the hydrolysis solution was passed through a C-18 Sep-pak column, followed in series by a 30 cm×7 mm i.d. econo-column (Bio-Rad) packed with 2 cm of DOWEX AG50W-X8 (100–200 mesh) resin in the hydrogen form and 16 cm of DOWEX AG1-X8 (200–400 mesh) resin in the carbonate form, and finally a neutral alumina Sep-pak. The liquid eluate was collected as waste. The final $^{18}$FDG product was then eluted off the column using 10 mL of water.

Synthesis times for manual manipulation of liquids with this cell averaged about 30 minutes. (This time can be reduced slightly with full automation of the process steps.) EOS yields as high as 62% (EOB) have been obtained although they typically range around 45% owing to product loss during purification and final formulation. (This final step in the process can also be refined for optimized product recovery.) Radiochemical purity of the final formulation generally exceeds 98%.

The shorter reaction times obtained using the apparatus and method of the invention are attributed to the greater efficiency of this apparatus for heating liquids in the optical cell during both the drying and reaction steps. The overall higher radiochemical yields in our tests can be traced to the nucleophilic substitution step involving [$^{18}$F]fluoride where on average 83%±9% of the fluoride reacts. This is significantly higher than is possible using present commercial reaction systems.

EXAMPLE 5

A synthesis of $^{18}$FDG was performed substantially as described in Example 4, except that the radiant energy emitted by the light source was focused in the reaction cell. This was accomplished by lowering the lamp toward the cell by an amount sufficient to place the focal point of the lamp in the center of the liquid residing in the cell (i.e., about 5 mm). The $^{18}$FDG radiochemical yield was increased to 86% (decay corrected to EOB), and 62% (EOS) in the final formulation.

EXAMPLE 6

$^{18}$FDG was prepared using an optical reaction cell and infrared source according to the invention, using a method substantially as described in Example 4 above, except that a weight equivalent amount of tetrabutylammonium hydroxide was used as the phase transfer reagent (70 µL of a 40% solution in water to give ~28 mg of the reagent). The reaction produced $^{18}$FDG in a 32% radiochemical yield of 32% (decay corrected to EOB). This result is substantially higher than previously reported syntheses of $^{18}$FDG using tetrabutylammonium hydroxide as a phase transfer reagent.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

Brodack et al., *Appl. Radiat. Isot.,* 39(7):699–703 (1988)
Coenen, HH, VW Pike, G Stöcklin, and R Wagner, *Appl. Radiat. Isot.,* 38(8):605–610 (1987).
DeGrado, TR, *J. Label. Cmpds. Radiopharm.,* 29(9):989–995 (1991).
Hamacher, K, HH Coenen, and G Stöcklin, *J. Nucl. Med.,* 27:235–238 (1986).
Hamacher, K, G Blessing, and B Nebeling, *Appl. Radiat. Isot.,* 41(1):49–55 (1990).
Ido et al., *J. Org. Chem.,* 42–2341 (1977).
Ido et al., *J. Label. Cmpds. Radiopharm.,* 14:175 (1978).
Reddy, GN, M Haeberli, H-F Beer, and AP Schubiger, *Appl. Radiat. Isot.,* 44(4):645–649 (1993).

What is claimed is:

1. Apparatus for performing a chemical reaction, comprising:
    a) an optical reaction cell comprising:
        i) a reaction reservoir defining therein a reaction volume capable of containing a reaction medium, and
        ii) an optical window which is substantially transmissive to infrared radiant energy capable of inducing a chemical reaction and which is positioned to permit direct coupling of infrared radiant energy with a reaction medium the reaction volume; and
    b) a radiant energy supply, comprising an infrared source capable of emitting broadband infrared radiant energy sufficient to induce and initiate a chemical reaction, wherein the radiant energy supply is positioned to directly couple emitted infrared radiant energy with a reaction medium in the reaction volume through the optical window.

2. Apparatus according to claim 1, wherein the infrared source emits radiant energy having wavelengths of from about 0.2 µm to about 2.5 µm.

3. Apparatus according to claim 2, wherein the infrared source emits radiant energy having wavelengths of from about 1.4 µm to about 1.9 µm.

4. Apparatus according to claim 1, wherein the infrared source comprises a quartz tungsten halogen lamp.

5. Apparatus according to claim 1, wherein the radiant energy supply further comprises an infrared reflector positioned to reflect infrared radiant energy emitted from the infrared source into the reaction volume.

6. Apparatus according to claim 5, wherein the reflector collimates or focuses reflected infrared radiant energy into the reaction volume.

7. Apparatus according to claim 6, wherein the reflector has a reflecting surface which describes an ellipsoidal or parabolic shape.

8. Apparatus according to claim 5, wherein the reflector has a reflecting surface comprising gold.

9. Apparatus according to claim 1, wherein the reaction reservoir is substantially inert to a reaction medium in the reaction volume.

10. Apparatus according to claim 1, wherein the reaction reservoir has an infrared-reflecting surface which is highly reflective to infrared radiant energy passing through the reaction volume.

11. Apparatus according to claim 1, wherein the reaction reservoir comprises platinum.

12. Apparatus according to claim 1, wherein the optical window comprises quartz.

13. Apparatus according to claim 1, wherein the optical reaction cell is sealable to prevent release of the reaction medium from the reaction volume.

14. Apparatus according to claim 1, wherein the apparatus further comprises a sealable conduit permitting controllable fluid communication with the reaction volume.

15. Apparatus according to claim 1, further comprising a temperature thermocouple for measuring temperatures within the reaction reservoir.

16. Apparatus according to claim 15, wherein an output from the temperature thermocouple is electrically connected to a control input of the radiant energy supply to permit temperature-dependent feedback control of radiant energy emission by the radiant energy supply.

17. Apparatus according to claim 1, where the chemical reaction is an endothermic chemical reaction.

18. Apparatus according to claim 17, wherein the chemical reaction is a nucleophilic substitution reaction.

19. Apparatus according to claim 18, wherein the chemical reaction is a nucleophilic fluorination reaction.

20. Apparatus for synthesizing a chemical compound by a chemical reaction, comprising:
    a) a reaction reservoir comprising a reaction volume for containing a reaction medium;
    b) a radiant energy supply, comprising an infrared source for emitting broadband infrared radiant energy sufficient to induce a chemical reaction; and
    c) an optical window substantially transmissive to infrared radiant energy sufficient to induce and initiate an endothermic chemical reaction, wherein the reaction reservoir, the radiant energy supply and the optical window are mutually positioned to permit direct coupling of infrared radiant energy emitted from the infrared source, through the optical window, into a reaction medium in the reaction volume, for inducing and initiating an endothermic chemical reaction.

21. Reaction apparatus for making a fluorinated compound by a nucleophilic fluorination reaction, comprising:
    an optical cell, which defines therein a reaction volume for containing a fluorination reaction medium, and which comprises an infrared-transparent window through which infrared radiant energy can be directly coupled with a fluorination reaction medium in the reaction volume, attached thereto via a pressure seal;
    a temperature thermocouple fitted to the optical cell for measuring temperature in the reaction reservoir;
    at least one fluid conduit for controllably transferring fluid into or out of the reaction reservoir;
    a vent port for controllably releasing pressure from the reaction reservoir;
    an infrared radiant energy supply positioned to directly couple sufficient broadband infrared radiant energy with the reaction volume, through the infrared-transparent window, to induce a nucleophilic fluorination reaction, wherein the infrared radiant energy supply comprises an infrared source for emitting broadband infrared radiant energy, and a reflector for reflecting infrared radiant energy emitted from the infrared source into the reaction volume.

22. A method for making 2-[$^{18}$F]fluoro-2-deoxy-D-glucose, comprising:

providing a reaction medium comprising [$^{18}$F]fluoride, a mannose derivative susceptible to nucleophilic fluorination reaction, and an inert solvent in an optical reaction cell adapted to admit infrared radiant energy;

reacting the [$^{18}$F]fluoride and the mannose derivative in the optical reaction cell by directly coupling broadband infrared radiant energy emitted from an infrared source with the reaction medium to provide an intermediate product by nucleophilic substitution;

evaporating the inert solvent from the reaction medium; and hydrolyzing the resulting intermediate product by contacting the intermediate product with a hydrolyzing agent in an aqueous medium to remove protective groups from the intermediate product to provide a hydrolysis product comprising 2-[$^{18}$F]fluoro-2-deoxy-D-glucose.

23. A method according to claim 22, wherein the reaction medium further comprises a phase transfer reagent.

24. A method according to claim 23, wherein the phase transfer reagent comprises a mixture of an aminopolyether and an alkali metal carbonate, a tetralkylammonium hydroxide, a mixture of a tetralkylammonium hydroxide and an alkali metal carbonate, a tetralkylammonium carbonate, or a tetraalkylammonium bicarbonate.

25. A method according to claim 24, wherein the phase transfer reagent comprises 4,7,13,16,24-hexaoxa-1,10-diazobicyclo(8.8.8)-hexacosane and potassium carbonate.

26. A method according to claim 22, wherein the [$^{18}$F] fluoride is provided as [$^{18}$F]CsF, [$^{18}$F]RbF, or [$^{18}$F]KF.

27. A method according to claim 22, wherein the mannose derivative is 1,3,4,6-tetra-O-acetyl-2-O-trifluoromethanesulfonyl-D-mannopyranose, methyl 4,6-O-benzylidene-3-O-methyl-2-O-trifluoromethanesulfonyl-β-D-mannopyranoside, a 2,3-O-cyclic sulfate of 1-O-methyl-4,6-benzylidene-β-D-mannopyranoside, 1,6-anhydro-3,4-di-O-benzyl-2-O-triflyl-β-D-mannopyranose, or 1,2-anhydro-3,4,5,6-di-O-isopropylidene-1-C-nitro-D-mannitol.

28. A method according to claim 22, wherein the hydrolyzing comprises:

reacting the intermediate product with the hydrolyzing agent in aqueous medium under reflux conditions by directly coupling infrared radiant energy emitted from the infrared source with the aqueous medium.

29. A method according to claim 22, wherein the hydrolyzing agent is a hydrogen halide.

30. A method for preparing a fluorinated compound, comprising:

performing a nucleophilic fluorination reaction in an optical reactor comprising:
 a) an optical reaction cell comprising:
  i) a reaction reservoir defining therein a reaction volume containing a reaction medium for conducting the nucleophilic fluorination reaction, and
  ii) an optical window which is substantially transmissive to infrared radiant energy capable of inducing the nucleophilic fluorination reaction and which is positioned to permit direct coupling of infrared radiant energy with the reaction medium in the reaction volume; and
 b) a radiant energy supply, comprising an infrared source capable of emitting broadband infrared radiant energy sufficient to induce the nucleophilic fluorination reaction, wherein the radiant energy supply is positioned to directly couple emitted infrared radiant energy with the reaction medium through the optical window.

31. A method according to claim 30, wherein the nucleophilic fluorination reaction comprises fluorinating using an [$^{18}$F]-containing reagent, and wherein the resulting fluorinated compound is an [$^{18}$F]-fluorinated radiotracer compound.

32. A method according to claim 30, wherein the nucleophilic fluorination reaction is a no-carrier-added nucleophilic radiofluorination reaction for production of [$^{18}$F] FDM, [$^{18}$F]FEDM, [$^{18}$F]-N-methylspiperone, [$^{18}$F]FDG, or [$^{18}$F]FDOPA.

* * * * *